United States Patent
Sims et al.

(10) Patent No.: US 6,494,938 B2
(45) Date of Patent: Dec. 17, 2002

(54) VACUUM DEGASSING

(75) Inventors: Carl W. Sims, St. Paul, MN (US); Yuri Gerner, Mendota Heights, MN (US); Kurt P. Hamberg, Fridley, MN (US)

(73) Assignee: Systec, Inc., New Brighton, MN (US)

(*) Notice: Subject to any disclaimer, the term of this patent is extended or adjusted under 35 U.S.C. 154(b) by 0 days.

(21) Appl. No.: 09/735,333

(22) Filed: Dec. 12, 2000

(65) Prior Publication Data

US 2001/0037731 A1 Nov. 8, 2001

Related U.S. Application Data

(63) Continuation-in-part of application No. 09/378,592, filed on Aug. 20, 1999, now Pat. No. 6,248,157.

(51) Int. Cl.[7] .............................................. B01D 19/00
(52) U.S. Cl. ........................................ 96/6; 96/8; 96/10
(58) Field of Search .............................. 95/46; 96/6, 8, 96/10

(56) References Cited

U.S. PATENT DOCUMENTS

| | | | |
|---|---|---|---|
| 3,668,837 A | | 6/1972 | Gross |
| 3,751,879 A | * | 8/1973 | Allington ...................... 96/6 X |
| 4,133,767 A | | 1/1979 | Bakalyar et al. |
| 4,325,715 A | * | 4/1982 | Bowman et al. ................. 96/6 |
| 4,430,098 A | | 2/1984 | Bowman et al. |
| 4,469,495 A | * | 9/1984 | Hiraizumi et al. ............... 96/6 |
| 4,729,773 A | * | 3/1988 | Shirato et al. ................... 96/6 |
| 4,834,877 A | * | 5/1989 | Peters et al. .................. 96/6 X |
| 4,986,837 A | * | 1/1991 | Shibata ............................ 96/6 |
| 4,994,180 A | | 2/1991 | Sims et al. |
| 5,183,486 A | | 2/1993 | Gatten et al. |
| 5,205,844 A | * | 4/1993 | Morikawa ......................... 96/6 |
| 5,290,340 A | * | 3/1994 | Gatten et al. ................. 96/6 X |
| 5,340,384 A | | 8/1994 | Sims et al. |
| 5,383,483 A | * | 1/1995 | Shibano ........................ 96/6 X |
| 5,425,803 A | * | 6/1995 | Van Schravendijk et al. . 96/6 X |
| 5,584,914 A | * | 12/1996 | Senoo et al. ...................... 96/6 |
| 5,762,684 A | * | 6/1998 | Hayashi et al. ............... 96/6 X |
| 6,248,157 B1 | * | 6/2001 | Sims et al. ....................... 96/6 |

FOREIGN PATENT DOCUMENTS

| | | | | |
|---|---|---|---|---|
| JP | 03-221130 | * | 9/1991 | ...................... 96/6 |
| JP | 03-224602 | * | 10/1991 | ...................... 96/6 |
| JP | 05-068808 | * | 3/1993 | ...................... 96/6 |
| SU | 0871806 | * | 10/1981 | .................... 95/46 |

OTHER PUBLICATIONS

S. R. Bakalyar et al., "The Role of Dissolved Gases in High–Performance Liquid Chromatography", *Journal of Chromatography*, 158 (1978) 277–293.

Ingo Pinnau et al., "Gas and Vapor Transport Properties of Amorphous Perfluorinated Copolymer Membranes Based on 2, 2–Bistrifluoromethyl–4,5–Difluoro–1, 3–dioxole/tetrafluoroethylene", *Journal of Membrane* Science 109 (1996) 125–133.

DuPont article, Teflon AF (amorphous fluoropolymers), Properties of Amorphous Fluoropolymers Based on 2,2–Bistrifluoromethyl–4,5–Difluoro–1,3–Dioxole, 183rd Meeting of Electrochemical Society, Honolulu, HI May 17, 1993.

Nemser, S., Applications of Membranes in Industry Glassy Fluoropolymer Membranes, 21 Aharon Katzir–Katchalsky Conference Rehovot, Israel, Sep. 5–8, 1993.

* cited by examiner

*Primary Examiner*—Robert H. Spitzer
(74) *Attorney, Agent, or Firm*—Haugen Law Firm PLLP

(57) ABSTRACT

A flow-through vacuum degassing unit for degassing a liquid includes a vacuum chamber adapted to be connected to a source for creating a vacuum in the chamber, an inlet and an outlet connection for admitting and discharging liquid to be degassed, a tube for conducting the liquid through the chamber, wherein the tube is a gas permeable polymeric resin material, and a control circuit for operating the source for creating a vacuum in the chamber responsive to a sensed vacuum level in the chamber.

4 Claims, 9 Drawing Sheets

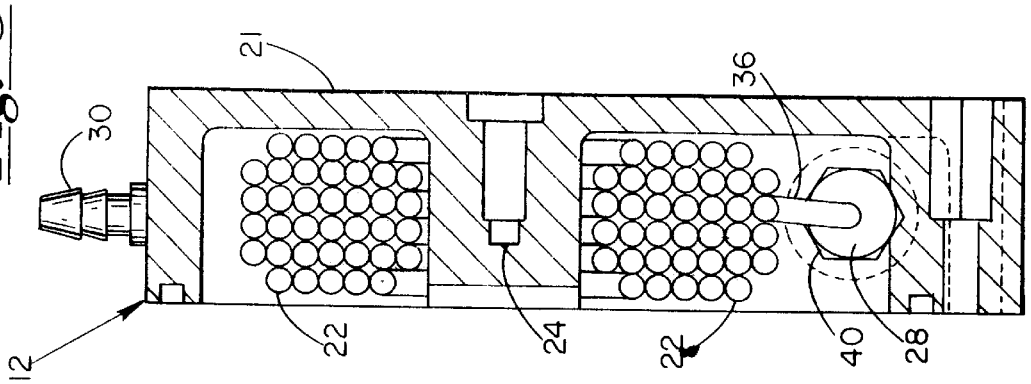
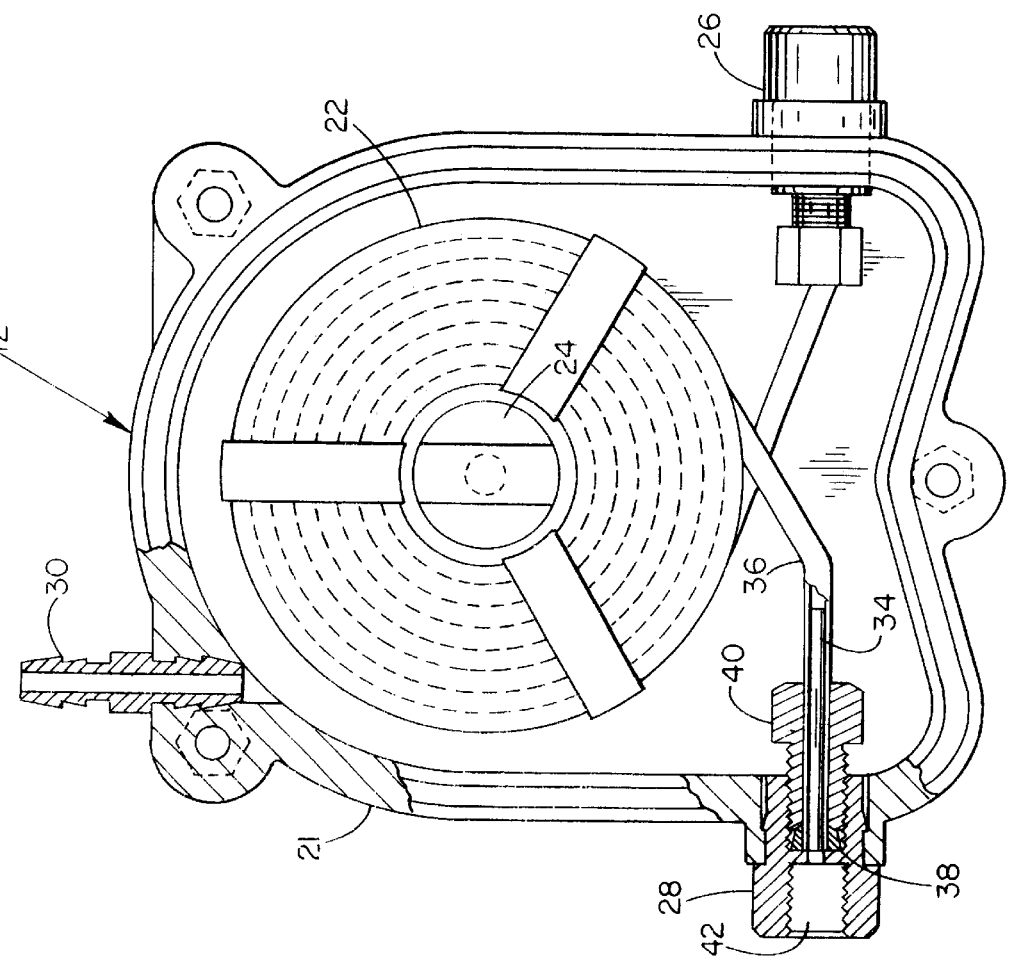

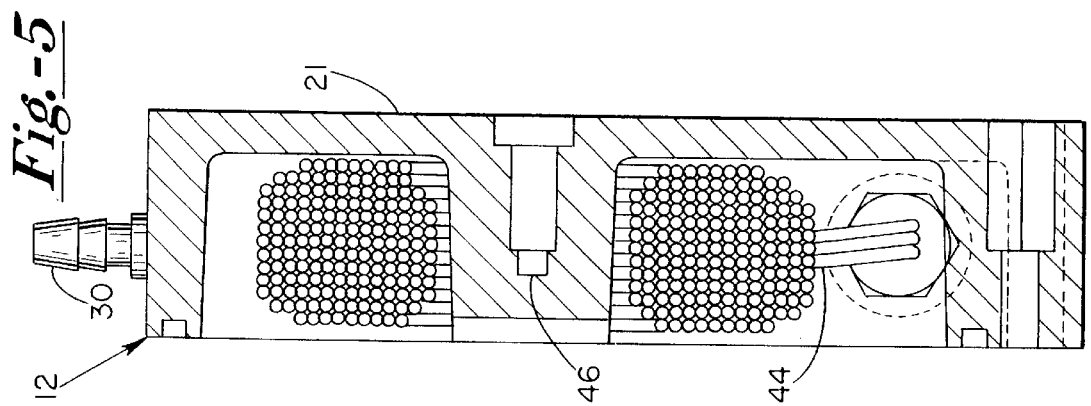
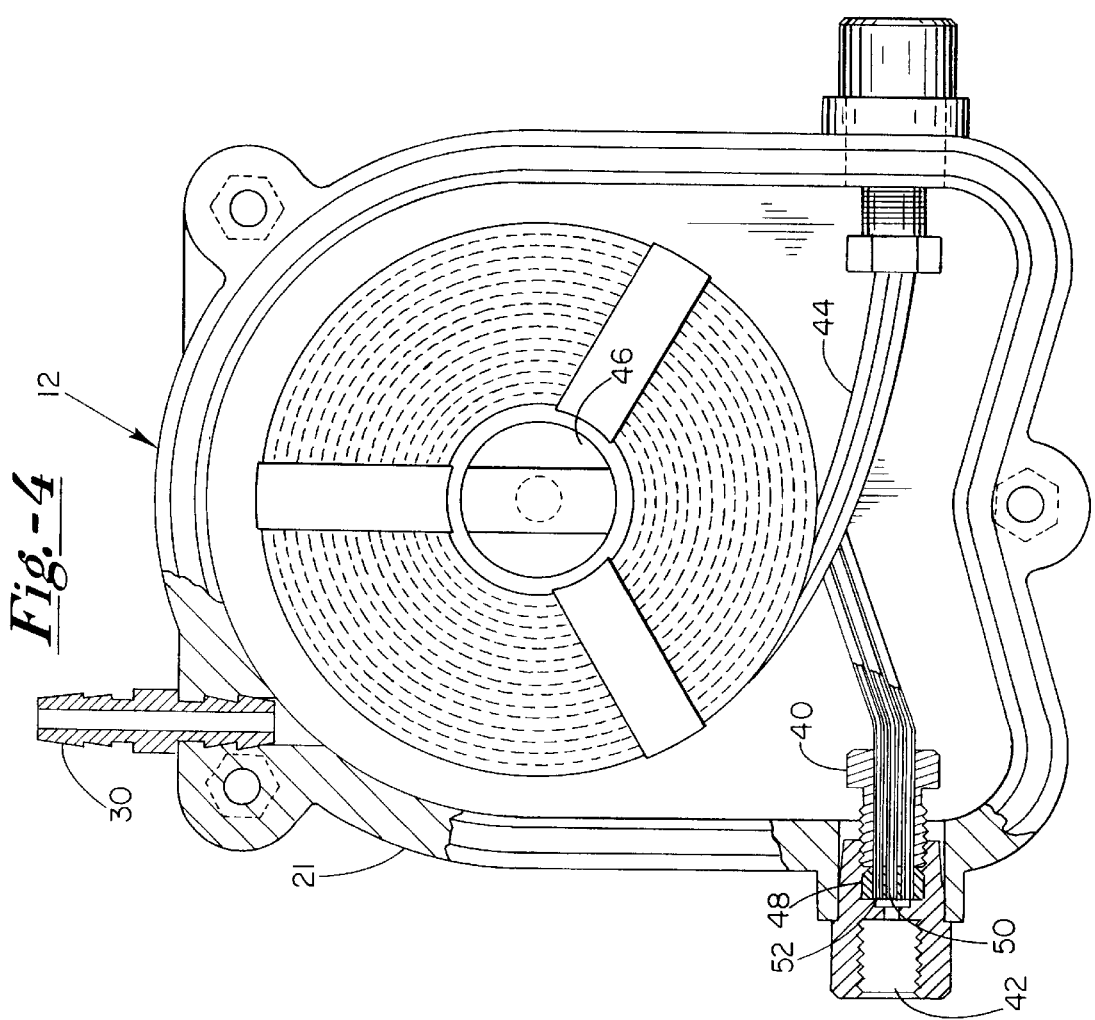

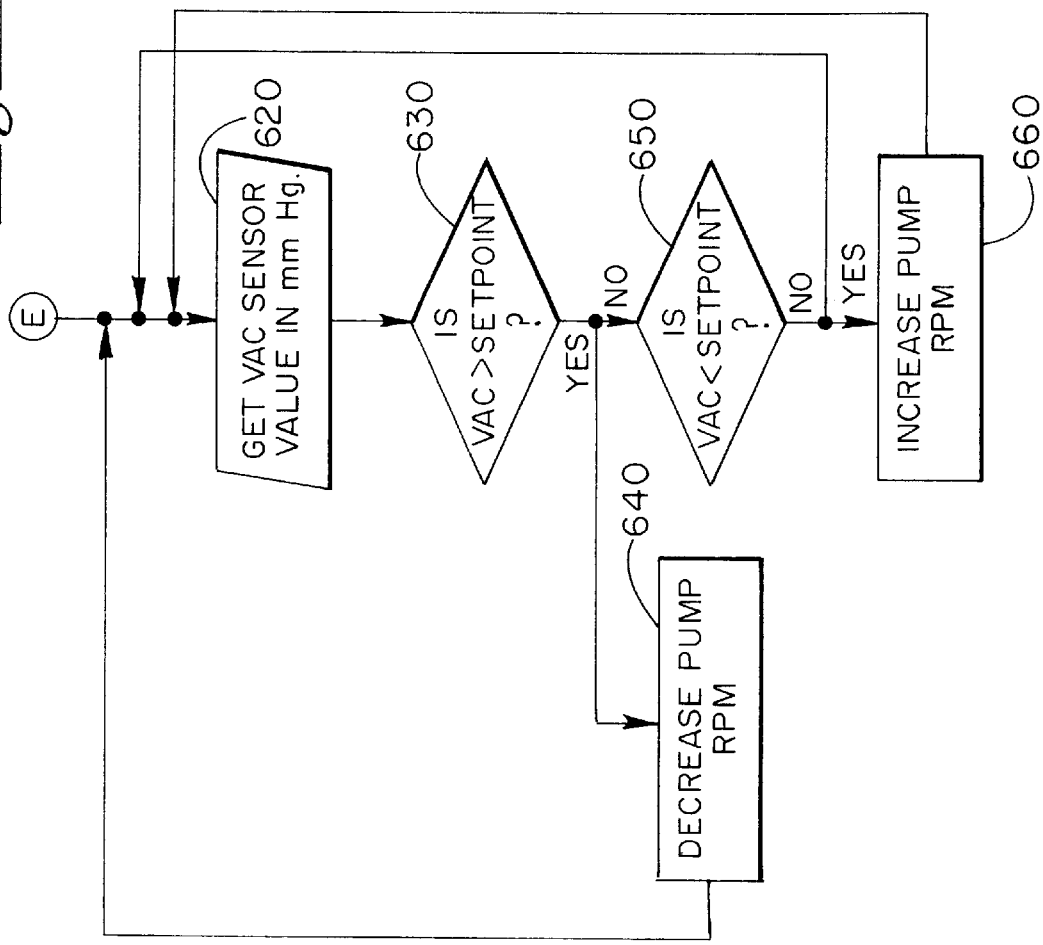

VACUUM DEGASSING

CROSS-REFERENCE TO RELATED APPLICATION

The present application is a continuation-in-part of our application Ser. No. 09/378,592, filed Aug. 20, 1999, entitled "VACUUM DEGASSING", now U.S. Pat. No. 6,248,157, and assigned to the same assignee as the present application.

BACKGROUND OF THE INVENTION

1. Field of the Invention

The present invention relates to a vacuum degassing system and more particularly pertains to a method and apparatus associated with removing gases from liquids in a flow-through relation in which an elongated gas-permeable tube addresses a vacuum chamber evacuated by a variable speed vacuum pump and gas is transferred by diffusion through the walls of the tube. The system is particularly suited to the removal of air or oxygen from the mobile phase associated with high performance liquid chromatographic equipment.

2. Description of the Prior Art

There are many chemical applications, particularly analytical applications, involving the use of liquid solvents, reactants or the like in which the presence of dissolved gases, particularly air, is undesirable. A prime example of such an application relates to the mobile phase in high performance liquid chromatography where the presence of even small amounts of dissolved gases, and in particular oxygen, interferes with the accuracy and sensitivity of the results obtained. For example, air dissolved in the mobile phase can manifest itself in the form of bubbles which causes noise and drift as the mobile phase passes through the detector. If the dissolved species be chemically active, as in the case of oxygen in air, it can additionally produce unwanted changes or deterioration in the mobile phase. Of course, the detrimental effect of the dissolved species is related to the relative concentration of the species in the mobile phase. These undesirable species usually are removed by a degassing process. It correspondingly follows that the more efficient the removal or degassing system is, the more desirable it will be.

The degassing of liquid materials has been necessary to the success of many processes and, consequently, the process has been pursued actively in several forms for a long period of time. Techniques have included heating or boiling the liquid to be degassed, exposing the material to a reduced pressure environment or vacuum and using combinations of heat and vacuum to reduce the amount of dissolved gases in the liquid. Ultrasonic energy has also been employed. As conventionally applied, however, these traditional techniques have generally fallen short of the desired degree of separation efficiency. Additionally, a means of degassing solvent involving the passing of a fine stream of bubbles of inert gas such as helium through the solution to be degassed has been shown by Bakalyar et al. in U.S. Pat. No. 4,133,767, and in apparatus such as that disclosed by Sims et al. in U.S. Pat. No. 4,994,180, co-invented by the co-inventor in the present application and assigned to the same assignee as the present invention.

Vacuum degassing through a membrane apparatus has long been known, and generally utilizes a length of relatively small diameter, thin-walled semi-permeable synthetic polymer resin material contained within an enclosed chamber held under a reduced pressure or vacuum in which the liquid to be degassified is caused to flow through the tube. One such apparatus is shown by Sims in U.S. Pat. No. 5,340,384, co-invented by the co-inventor in the present application and assigned to the same assignee as the present invention. Other such devices are shown in U.S. Pat. Nos. 5,183,486, 4,430,098, and 3,668,837.

While each of these devices employ a flow-through tube vacuum degassing approach, there remains a need, particularly with devices associated with high performance liquid chromatography instruments, to make degassing of solvents, and in particular the mobile phase, more efficient. One particular limitation or drawback associated with present devices concerns the efficiency of the degassification operation with respect to the composition of the tubing itself. Materials presently used in degassing applications include PTFE, PFA, and silicone rubber. These materials, while generally suitable for this application, require that the wall thickness be as thin as possible due to the gas permeability of materials typically utilized for these applications. A large internal diameter tube is disadvantageous as the gas must diffuse through a longer path from the center of the flow to the inner wall surface, thereby requiring a long tube. Additionally, a tube of greater length increases flow resistance through the overall system the resistance being a linear function of tubing length (assuming laminar liquid flow through the tubing). Liquid flow resistance is an inverse function of tubing internal diameter to the fourth power.

Amorphous perfluorinated copolymers reportedly have permeabilities of up to 2 or 3 orders of magnitude higher than those of PTFE. It has been found by the present inventors that by using amorphous perfluorinated copolymers, such as those marketed by Du Pont under the tradename Teflon AF that permeabilities of up to about 1 order of magnitude or greater are experienced. Nevertheless, in the fabrication of degassing tubes, greater gas mass transfer rates can be achieved with tubes of Teflon AF having increased wall thicknesses, thereby permitting the undertaking of applications requiring higher pressures. Advantageously, tubes of smaller internal diameter and shorter length offer reduced internal volumes. Low flow resistance is accomplished with multi-lumen tubing arrangements.

Because of the enhanced gas permeability property of materials utilized in accordance with the present invention, the diffusion rate of atmospheric gases from the liquid being degassed through the tubing wall is significantly increased. It appears likely that the increased gas permeability is enhanced by the free (void) volume in the polymer component.

As a further feature of this invention, it has been found that very stable reduced pressure or vacuum is achieved within the vacuum chamber. This feature is possible due to the operational characteristics of the vacuum pump. In initial operation, the pump (typically operated @ 400 RPM) reduces pressure inside the vacuum chamber. When the pressure inside the chamber begins to asymptotically approach a maximum differential value (typically around 60 mm Hg absolute) the speed is substantially reduced, such as to bout 60 RPM. The pump is run continuously at this reduced rate, with the vacuum then slowly descending to a "constant vacuum level" with the pressure remaining constant for so long as the pump is running. This "constant vacuum level" provides significant advantages in that it eliminates vacuum (pressure) hysteresis which typically is in the range of 15–25 mm Hg as the result of cycling the pump on and off as in other systems. Through this operational feature, variations in remaining atmospheric gas in the mobile phase exiting the degassing apparatus to the liquid chromatograph are also eliminated. This feature provides technical advantages because of the resulting HPLC detector base line stability. Superior vacuum level, typically in the range of 30 mm Hg or less, also reduces the absolute concentration of dissolved gases in the mobile phase, which improves the flow rate precision of the HPLC pump. In addition, longer life expectancy of the vacuum pump is achieved because of low RPM.

Accordingly, it is a principal object of the present invention to provide a more efficient vacuum degassing system of the flow-through type using a tube or multiple tubes formed from an amorphous perfluorinated copolymer.

A further object of the present invention is to reduce the required inside diameter and length of the degassing tube.

A still further object of the present invention is the provision of a tube having a single lumen.

A yet further object of the present invention is the provision of a tube having multiple lumen.

Another object of the present invention is the provision of a variable speed pump which is run continuously for evacuating the vacuum chamber, with the effects being a reduction or elimination of hysteresis and increased vacuum pump life expectancy.

Still further object of the present invention is the utilization of a flow restrictor in the system to facilitate bleeding or flushing of the head with atmosphere to prevent solvent vapor build up.

Still another object of the present invention is to provide a means for interconnecting liquid chromatography instrument components which simultaneously degasses the mobile phase in transit between the components.

It is yet a further object of the present invention to provide an improved vacuum pump head bleed or flush system in the form of a vent frit including a sintered metal plug, thereby eliminating the necessity of the solenoid operated vent valve typically utilized in current systems.

A still further object of the invention is to provide an improved connection system for the tube associated with a flow-through vacuum degassing apparatus.

SUMMARY OF THE INVENTION

By means of the present invention, the efficiency of a flow-through vacuum degassing system utilizing an elongated gas-permeable tube is improved by reducing the required inside diameter and length of the tube. This is achieved by forming the tube from an amorphous perfluorinated copolymer such as Teflon AF. Amorphous perfluorinated copolymers have been reported to have permeabilities of up to 2 or 3 orders of magnitude greater than other semipermeable polymeric resins utilized in degassing applications. By using such copolymers, it has been found that it is possible to significantly reduce the length of tubing utilized, which correspondingly and proportionally reduces the internal volume. All of this is achieved without either reduction or compromise in degassing performance.

Gas mass transfer rates are further improved by the present invention through the use of a tube having multiple lumen. The multiple lumen tubing arrangement offers greater degassing efficiency by providing a greater surface area through which the gas may travel and a smaller tubing diameter. A multiple lumen tubing of smaller diameter provides for reduced internal volume and lower flow resistance to the mobile phase sought to be degassed.

The degassing chamber of the invention includes an injection-molded plastic housing which is preferably sealed with o-rings or other sealing devices. The chamber is provided with a vacuum connection and liquid inlet and outlet connections for a coil of gas-permeable tubing. The coil may be either a single lumen tube or a multiple lumen tube. A pair of interface grids each positioned between a bulkhead fitting and an inlet or outlet nut is fabricated of TEFZEL®, KEL-F, PTFE or PEEK for use with the multiple lumen tube and includes a center bore and a plurality of radially spaced bores for sealingly receiving the tubes in an adhesiveless manner when they are pulled through during assembly of the degassing chamber. Teflon AF tubing may be advantageously utilized, when placed through a slightly over-sized hole, with the tubing being pushed through and compressed on the ferrule with a nut. Compression seals utilizing TEFZEL® ferrules have been found highly useful and are preferred in creating seals without requiring adhesives.

In an alternative embodiment of the invention, a degassing transfer line for interconnecting liquid chromatography system components includes a length of Teflon AF tubing extending between opposed ends of the transfer line and disposed within an elongate tube formed of an adhesive-lined, heat shrinkable material, with this alternative embodiment being described in detail herein. In this alternative embodiment, opposed ends of the tube sealingly surround a PTFE/FEP dual-shrink tubing through which the Teflon AF tubing extends. Distally of each opposed end of the elongate tube, a nut is sealingly attached to the PTFE/FEP tubing. Distally of the nut, ferrules are provided for connection to the various LC components. A vacuum adapter is provided for communication between an interior of the elongate tube and a vacuum source to evacuate the interior of the elongate tube and thereby degassing the mobile phase as it flows through the Teflon AF tubing.

Another feature of the present invention provides for a variable speed vacuum pump which evacuates the vacuum chamber. In a first preferred mode of operation, electronic control means responsive to a sensed vacuum level are operable to drive a variable-speed motor which in turn drives an eccentric shaft coupled to a two-stage diaphragm pumping mechanism at a high speed to quickly evacuate the vacuum chamber (400 RPM) and at a low speed, such as about 60 RPM, for continuous operation and long life of the degassing system. In an alternative second mode of operation, a vacuum setpoint is set and the pump is intermittently driven at the high speed when the sensed pressure rises above the setpoint, with the rate dropping once the desired pressure reduction has been achieved. In an alternative third mode of operation, a sensed vacuum level is continuously compared to a vacuum setpoint to provide electronic control means with specified input to continuously control pump rpm so as to maintain a constant vacuum.

BRIEF DESCRIPTION OF THE DRAWINGS

In the drawings, wherein like numerals designate like parts throughout the same:

FIG. 2 is a cross sectional view of the vacuum chamber in accordance with the present invention showing a single lumen tube;

FIG. 3 is a cross sectional view of the vacuum chamber of FIG. 2;

FIG. 4 is a cross sectional view of the vacuum chamber in accordance with the present invention showing a multiple lumen tube;

FIG. 5 is a cross sectional view of the vacuum chamber of FIG. 4;

FIGS. 9A, 9B, 9C, and 9D are a flow chart showing the three modes of operation of the invention.

DETAILED DESCRIPTION OF THE PREFERRED EMBODIMENT

Figure 1:
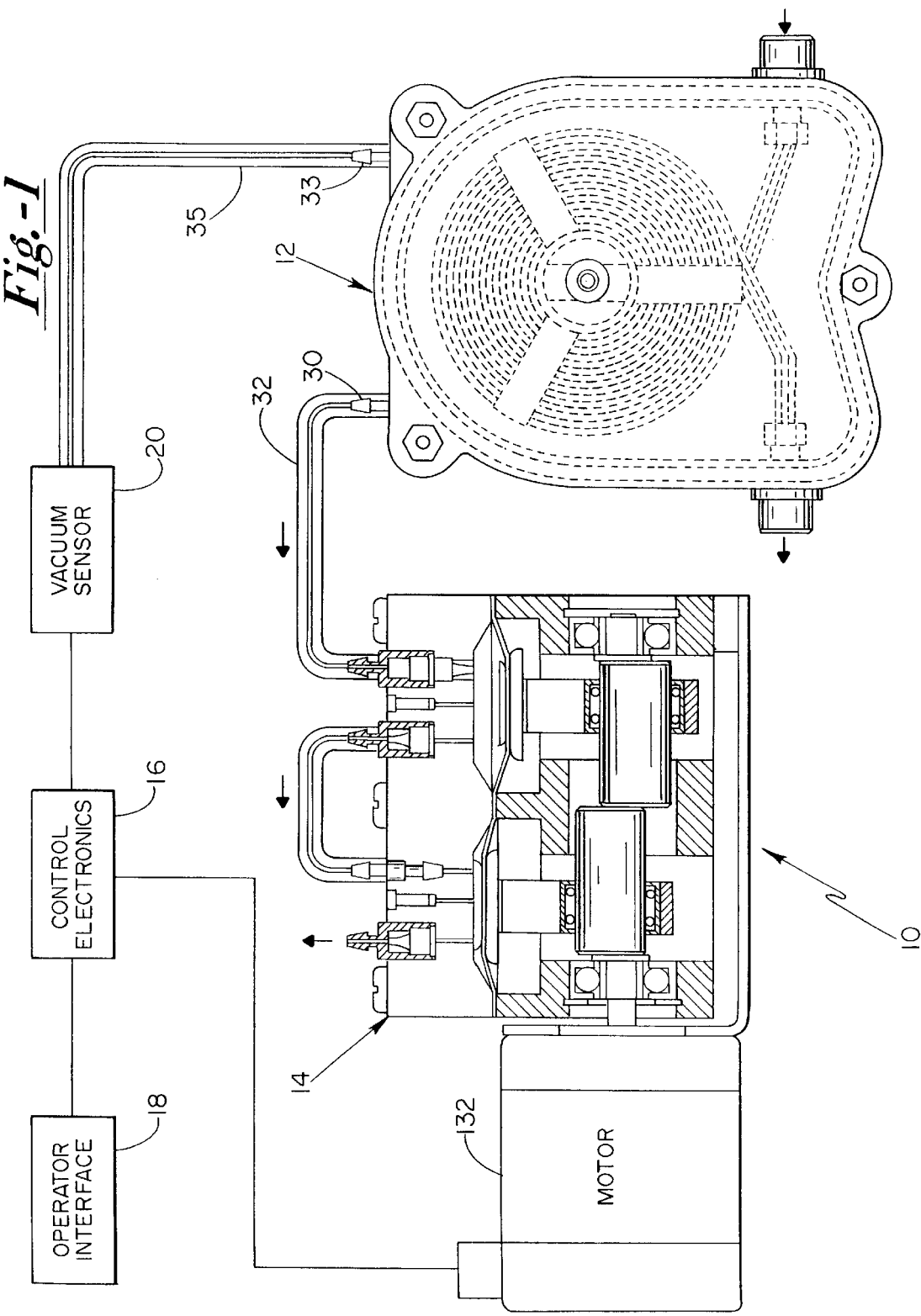
FIG. 1 is a schematic diagram showing the components of the present invention.

The objects and advantages enumerated above together with other objects, features and advances represented by the present invention will now be presented in terms of a detailed embodiment described with reference to the attached drawing Figures which are intended to be but representative of many possible configurations of the invention. Other embodiments and aspects of the invention are recognized as being within the grasp of those having ordinary skill in the art. With particular initial reference to FIG. 1, there is shown generally at 10 a vacuum degassing system having a vacuum chamber 12, a vacuum pump 14 and a vacuum sensor 20 operably coupled to the vacuum chamber 12, an electronic control means 16 operably coupled to the vacuum pump 14 and to the vacuum sensor 20, and an operator interface 18 operably coupled to the control means 16.

The vacuum chamber 12 is preferably made of high-impact polymer material, such as high-density polyethylene or polypropylene, which can be readily assembled with sealing o-rings or heat welded together to form a strong, relatively inert, non-metallic housing 21. A single lumen degassing tube is shown schematically in FIG. 2 at 22 as being loosely constrained by a central shaft or spool member 24 to form a coil. In the preferred embodiment the degassing tube is made from an amorphous perfluorinated copolymer such as Teflon AF. The tube 22 is connected between inlet and outlet connections 26 and 28. The vacuum chamber 12 further contains a connection as at 30 for a vacuum line 32, which is designed to be connected to the vacuum pump 14. Additionally, a connection as at 33 for a vacuum line 35 operably coupled to the vacuum sensor 20 is shown.

The inlet and outlet connections as at 26 and 28 include a short length of interface tubing 34 which may be high strength, high density, relatively inert material, such as PEEK or, if metal, titanium or stainless steel and having an end as at 36 over which the degassing tube 22 is fitted. The interface tube 34 is further connected using an appropriate sealing ferrule 38 which may be of TEFZEL® or other inert material used in conjunction with a nut 40 to connect to the bulkhead union 42.

In accordance with an important aspect of the invention, a multiple lumen tubing 44 made from Teflon AF is shown schematically in FIG. 4 at 44 as being loosely constrained by a central shaft or spool member 46 to form a coil. A pair of interface grids 48 preferably in a form of a TEFZEL® reverse or inverted ferrule, each positioned between a bulkhead fitting as at 42 and an inlet or outlet nut as at 40 is fabricated of stainless steel, KEL-F or PEEK for use with the multiple lumen tube 44 and includes a center bore 50 and a plurality of radially spaced bores 52 for sealingly receiving the tubes in an adhesiveless manner with nut 40 compressing reverse or inverted ferrule 48 when the tubes are pulled through during assembly of the degassing chamber 12.

Figure 6:
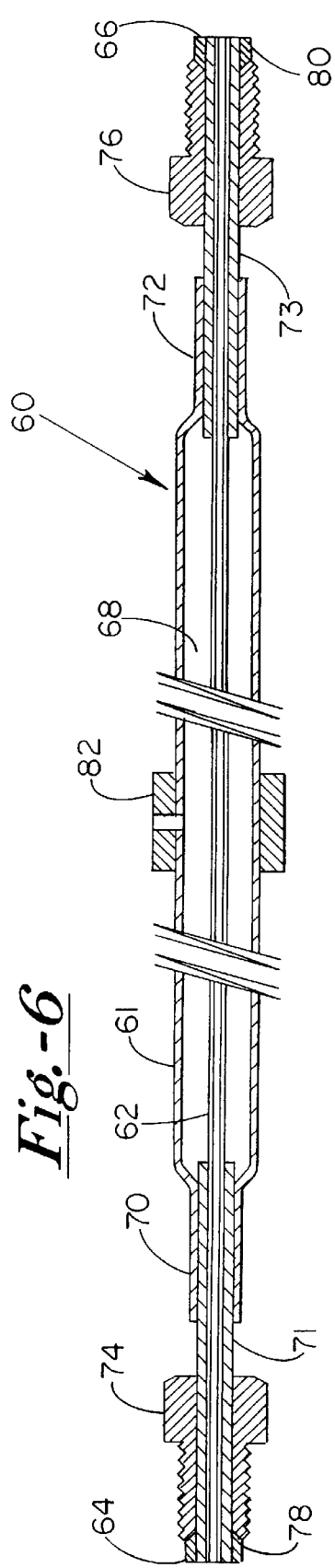
FIG. 6 is a cross sectional view of a transfer line having a single lumen according to the present invention.

With reference to FIG. 6, an alternative embodiment of the present invention generally designated 60 is shown. The alternative embodiment 60 comprises a degassing transfer line in the form of an elongate tube 61 for use in interconnecting liquid chromatography system components. A length of gas permeable tube 62, preferably Teflon AF, extends between opposite ends 64 and 66 of the transfer line. An enclosed interior portion 68 of the elongate tube 61 is formed by sealing opposed ends 70 and 72 of an adhesive-lined, heat shrinkable material about spaced sections of a PTFE/FEP dual-shrink tubing 71 and 73 disposed in surrounding relationship to the tube 62. Distally of the opposed ends 70 and 72, a pair of nuts 74 and 76 in conjunction with a pair of ferrules 78 and 80 are formed in surrounding relationship to the tubing 71 and 73 for connecting the transfer line between liquid chromatography system components. A vacuum adapter 82 is provided for communication between the interior portion 68 of the elongate tube 61 and a vacuum source to evacuate the interior portion 68 and thereby degass the mobile phase as it flows through the tube 62.

Figure 7:
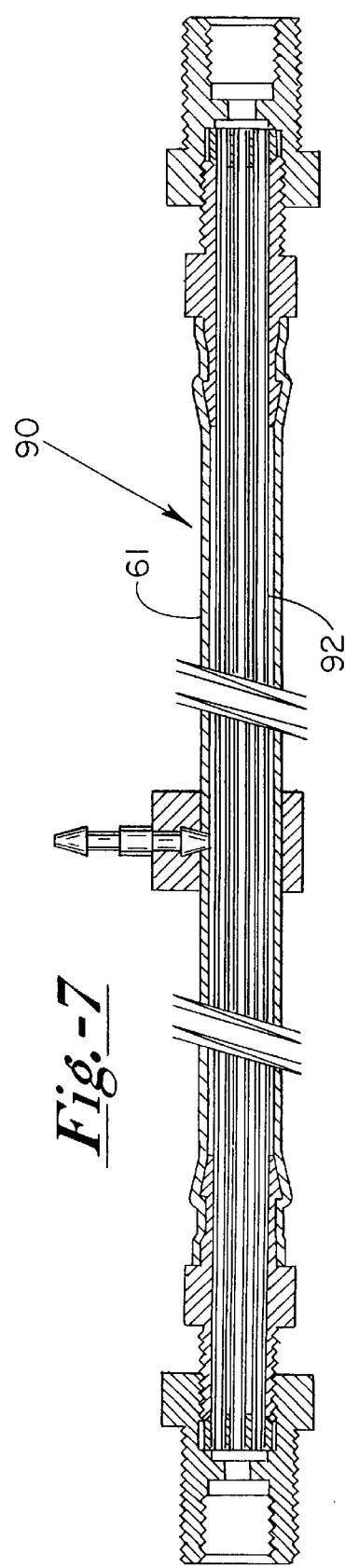
FIG. 7 is a cross sectional view of a transfer line having a multiple lumen according to the present invention.

An alternative embodiment of the transfer line is shown in FIG. 7 and generally designated 90. The degassing transfer line 90 is similar to the transfer line 60 but is provided with a multiple lumen tube 92 in place of the single lumen tube 62.

Figure 8:
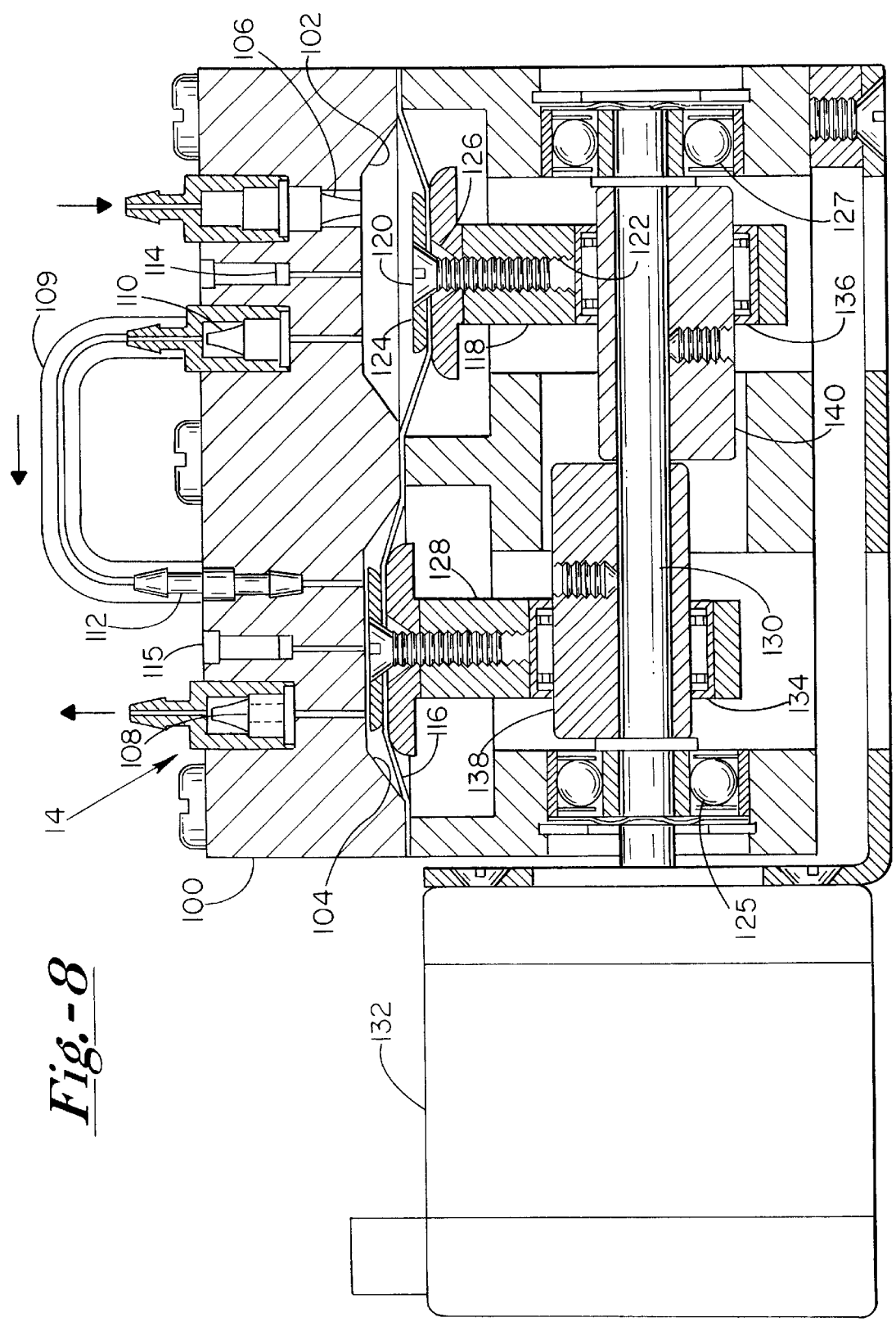
FIG. 8 is a cross sectional view of the vacuum pump of the present invention.

In accordance with another important aspect of the present invention, a variable speed vacuum pump 14 is operable in a first mode of operation to continuously evacuate the vacuum chamber 20 or to intermittently evacuate the vacuum chamber 20 in a second mode of operation. The vacuum pump 14 is shown in FIG. 8 and includes a two stage, series diaphragm pumping mechanism. A manifold 100 includes a first stage head 102 and a second stage head 104. The manifold further includes an intake duckbill check valve 106 associated with the first stage and an outtake duckbill check valve 108 associated with the second stage. The first and second stages are in fluid flow communication with each other through a tube 109 attached to the first stage through a duckbill check valve 110 and attached to the second stage through a barbed fitting 112. A vent frit including a sintered metal plug 114 provides a precise vent or bleed (precision flow restrictor from Mott metallurgical) to vent solvent vapors that may build up. Furthermore, the "precision leak" of the sintered metal plug advantageously replaces the solenoid operated vent valve which has been typically utilized. This bleed feature is normally placed in the first stage during the intake stroke thereof to prevent the buildup of vapor and to reduce the exposure of the pump diaphragm to degassed vapors entering the first stage and thereby reduce diaphragm and check-valve swelling and prolong the useful life of the vacuum pump 14. As further described hereinbelow, during the exhaust stroke of the first stage, the second stage is on its intake stroke which ensures very little leakage to the outside.

In a preferred embodiment of the present invention, a second vent frit including a sintered metal plug 115 is provided in the second stage of pump 14. The second vent frit 115 is included to vent any residual solvent vapors that may form in the second stage of pump 14, and in particular, at or near outtake check valve 108. As with vent frit 114, second vent frit 115 is placed in the second stage of pump 14 to provide a precision bleed function, thereby decreasing detrimental solvent condensation. Use of such vent frits 114, 115 preferably sweeps both first and second stage heads 102, 104 with fresh air to remove solvent condensation while having no major detrimental effect on the vacuum developed within pump 14. Such venting is particularly advantageous when utilizing solvents such as methylene chloride which have detrimental effects on respective transfer lines when in liquid (condensed) form.

A unitary diaphragm 116 extends from the first stage to the second stage. In the first stage, the diaphragm 116 is affixed to a rod 118 by means of a press fit pin or screw 120 received in a bore 122 formed in the rod 118. A washer 124 and 0-ring 126 seal the diaphragm 116 to the rod 118. The diaphragm 116 is affixed to a rod 128 in the second stage in a similar fashion. The diaphragm 116 is preferably formed of PTFE which is inert and tolerant to exposure to common liquid chromatography solvents and vapors thereby insuring the longevity of the diaphragm 116.

Rods 118 and 128 are shown connected to a shaft 130 coupled to a motor 132 at one end thereof. The shaft 130 is rotatably supported in a frame by means of spaced ball bearings 125 and 127. The rods 118 and 128 are connected to the shaft 130 by means of needle bearings 134 and 136 operably coupled to opposed eccentric portions 138 and 140 fixedly and spacedly attached to the shaft 130. By this arrangement, rotation of the shaft 130 results in reciprocal motion of the first and second stages 180 degrees out of phase with one another.

The motor 132 is preferably any variable-speed motor that is responsive to control means and provides for closed loop control thereof. Specific examples of such a motor 132 include brushless DC stepper motors, frequency modulated motors, and pulse width modulated motors. A pressure sensor 20 is operable to sense the vacuum level inside the vacuum chamber 12 and generate a voltage output which is ratiometric to the vacuum level and a supply voltage. The sensor output is amplified by an instrumentation amplifier and is then converted to a pulse width modulated signal which is sent to a microcontroller. A high-current pulse width modulated, uni-polar controller chip operably coupled to the microcontroller drives the motor 132 in such manner that in a first continuous mode of operation, the motor 132 runs at a high speed to quickly evacuate the vacuum chamber and at a low speed for continuous operation of the degassing system. A second intermittent mode of operation is provided wherein a vacuum setpoint is set and the pump is intermittently driven at the high speed when the sensed vacuum falls below the setpoint. A third continuous mode of operation provides continuous control of vacuum pump rpm by continuously adjusting motor rpm as a function of vacuum level to maintain a constant vacuum. Such a third continuous mode of operation preferably reduces hysteresis of sample measurements and enhances reproducability among distinct instruments utilizing vacuum pump 14.

Firmware embedded in the microcontroller of the present invention provides for a user interface allowing for selection of the modes of operation as shown at 170 in FIGS. 9A–9D. In the first continuous mode of operation (210), the vacuum level is optionally displayed (220). To indicate that the vacuum degassing system is not yet operable, "not ready" is displayed (230). A setpoint is then obtained for comparison to the vacuum level in the vacuum chamber 12 (240). The setpoint may be entered by the user or optionally programmed in the firmware. A pump down timer is next set for five minutes (250). The pump is then driven at the high speed to evacuate the vacuum chamber 12 (260). The vacuum sensor value is read (270) and if after a one second delay (280) it is less than the set point (290), the pump is driven at the high speed if the user has not changed the mode of operation (300). If the sensed vacuum is greater than the setpoint then the vacuum pump is driven at the lower speed and a value for a leak condition setpoint is read (310). The sensed vacuum value is then read (320) and if the value is less than the leak condition setpoint (330) "leak" is displayed to the user (360). If the sensed vacuum value is greater than the leak condition setpoint then a change in mode of operation is checked for (340). If the user has selected the second intermittent mode of operation, then the program jumps to (200). If the user has not changed the mode of operation then after a one second delay (350) the sensed vacuum value is again compared to the leak condition setpoint (330) and the loop is repeated until either the user selects a different mode of operation or the sensed vacuum level falls below the leak condition setpoint.

In the second intermittent mode of operation (400) the vacuum level option selected is displayed (410) and to indicate that the vacuum degassing system is not yet operable, "not ready" is displayed (420). A setpoint is then obtained for comparison to the vacuum level in the vacuum chamber 12 (430). The setpoint may be entered by the user or optionally programmed in the firmware. A pump down timer is next set for five minutes (440). The pump is then driven at the high speed to evacuate the vacuum chamber 12 (450). The vacuum sensor value is read (460) and if after a one second delay (470) it is less than the set point (480), the pump is driven at the high speed if the user has not changed the mode of operation (490). If the sensed vacuum is greater than the setpoint then the vacuum pump is turned off and a "ready" indication is displayed (500). A hysteresis value and a leakdown time are also read from memory (500). The sensed vacuum value is then read (510) and if the value is greater than the setpoint plus the hysteresis value (520) then the leakdown time is compared to a maximum leakdown time (550). If the sensed vacuum value is greater than the setpoint plus the hysteresis value a change of mode of operation is checked for (530). If the user has changed modes, then the system jumps to (170). If the user has not changed modes, then after a one second delay (540), the system loops back to (520) and the sensed vacuum value is again compared to the setpoint value plus the hysteresis value. If the sensed vacuum value is less than the setpoint plus the hysteresis value the leakdown time is compared to the maximum leakdown time (550). If the leakdown time is less than the maximum leakdown time a "leak" indication is displayed (560). If the leakdown time is greater than the maximum leakdown time the pump down time is set for one minute (570) and the system jumps to (450) to drive the pump at the high speed to evacuate the vacuum chamber 12 (450).

Figure 9A:
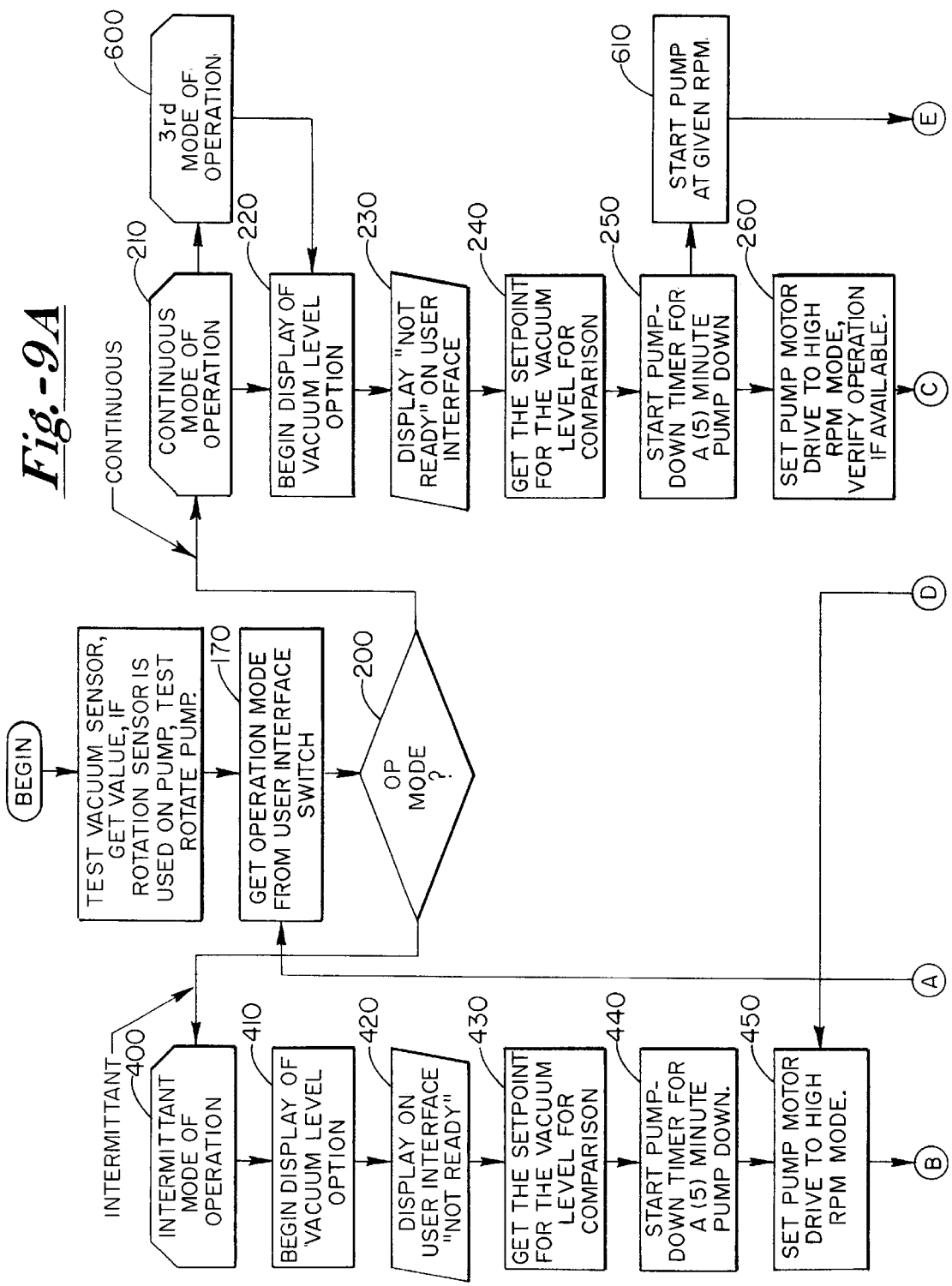
Figure 9B:
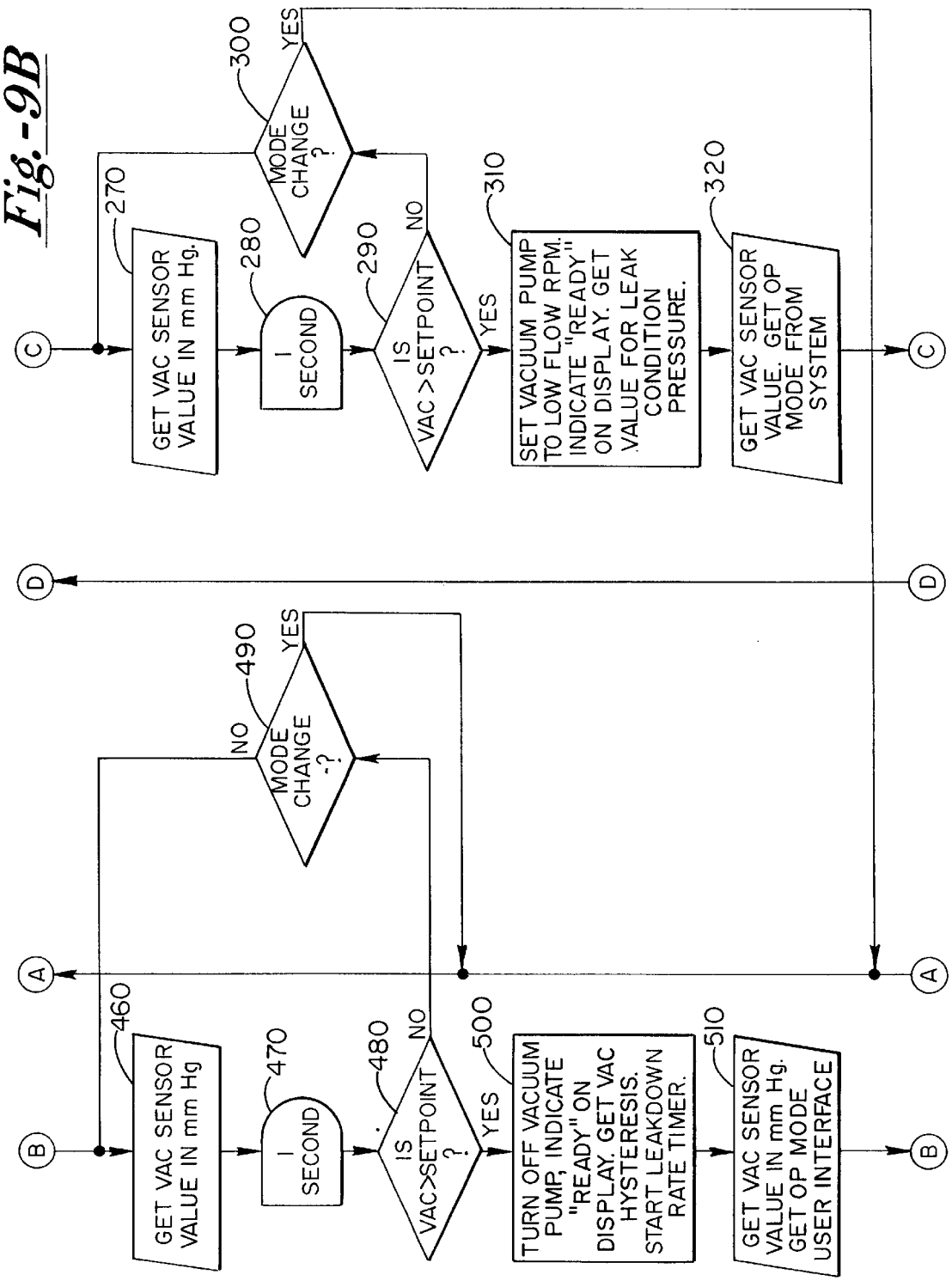
Figure 9C:
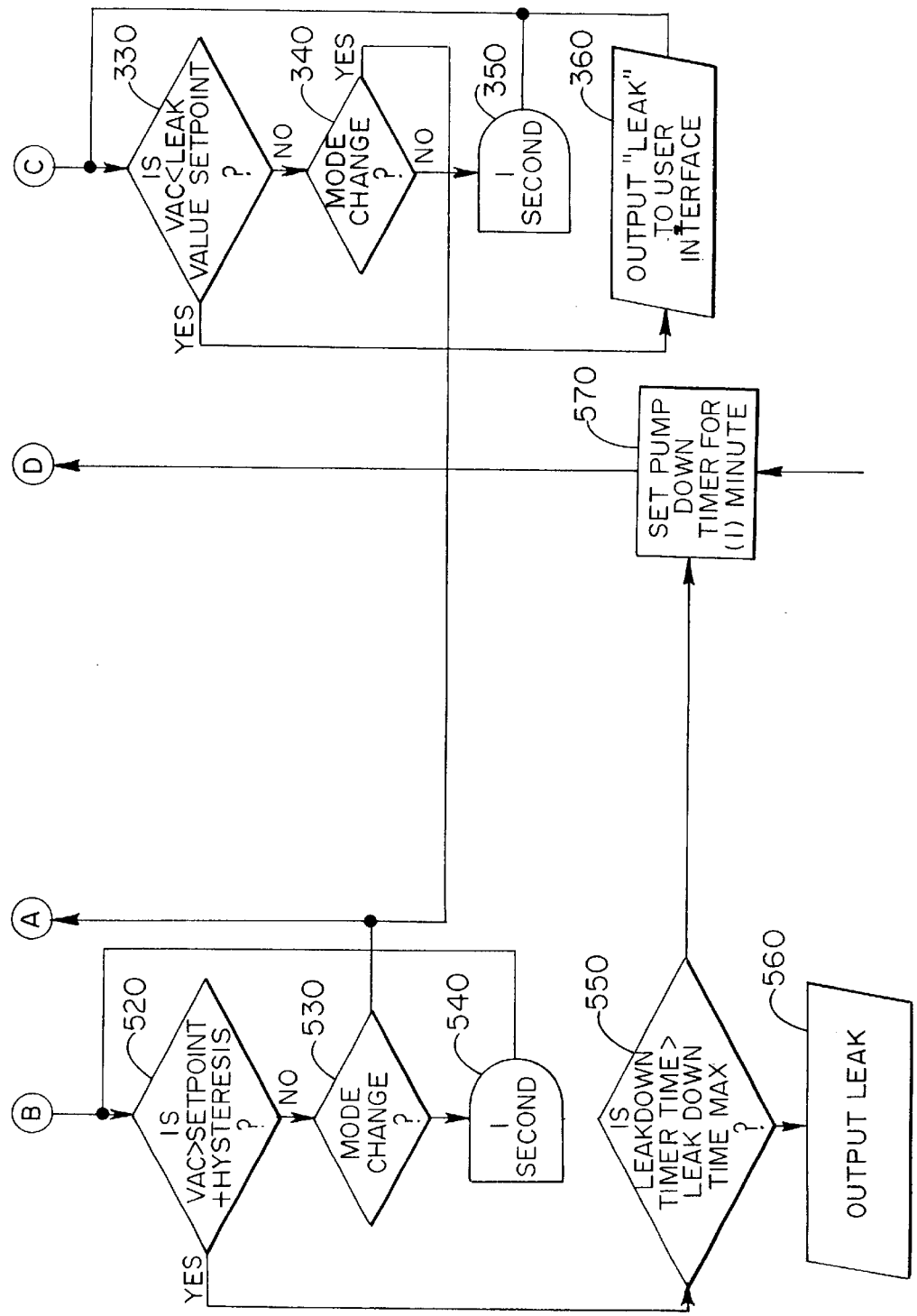

A third continuous mode of operation (600) preferably incorporates the initial steps of the first continuous mode of operation (210) as shown in FIG. 9A. After a vacuum setpoint has been entered by the user or optionally programmed in firmware, the pump is driven at a given start speed to evacuate vacuum chamber 12 (610). The vacuum sensor value is continuously read (620) and compared to the vacuum setpoint (630). If the vacuum sensor value is greater than the vacuum setpoint, the pump rpm is correspondingly reduced (640). If the vacuum sensor value is less than the vacuum setpoint (650), the pump rpm is correspondingly increased (660). Such a comparison process is continuously undertaken to maintain a constant vacuum.

The invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A flow-through vacuum degassing unit for degassing one or more liquids comprising:

a vacuum chamber adapted to be connected to a source for creating a vacuum in the chamber;

inlet and outlet connections for admitting and discharging liquid to be degassed;

a continuous tube for conducting the liquid through the chamber, the tube being connected between the inlet and the outlet connection and the tube being formed of a polymeric material permeable to pass dissolved gases therethrough but liquid impermeable; and control means for operating a two stage, series pump for creating a vacuum in the chamber responsive to a sensed vacuum level in the chamber, wherein a second stage of said pump is continuously vented through a sintered metal plug, with said control means being designed to operate said vacuum source at a relatively rapid rate during initial pump down, and being further adapted to operate said vacuum source at a substantially steady but lower rate after a desired level of vacuum has been achieved.

2. A flow-through vacuum degassing unit for degassing one or more liquids comprising:

a vacuum chamber adapted to be connected to a source for creating a vacuum in the chamber;

inlet and outlet connections for admitting and discharging liquid to be degassed;

a continuous tube for conducting the liquid through the chamber, the tube being connected between the inlet and the outlet connection and the tube being formed of a polymeric material permeable to pass dissolved gases therethrough but liquid impermeable; and control means for operating a two stage, series pump for creating a vacuum in the chamber responsive to a sensed vacuum level in the chamber, wherein both stages of said pump are continuously vented through sintered metal plugs, with said control means being designed to operate said vacuum source at a relatively rapid rate during initial pump down, and being further adapted to operate said vacuum source at a substantially steady but lower rate after a desired level of vacuum has been achieved.

3. A flow-through vacuum degassing unit for degassing one or more liquids comprising:

a vacuum chamber adapted to be connected to a source for creating a vacuum in the chamber;

inlet and outlet connections for admitting and discharging liquid to be degassed;

a continuous tube for conducting the liquid through the chamber, the tube being connected between the inlet and the outlet connection and the tube being formed of a polymeric material permeable to pass dissolved gases therethrough but liquid impermeable; and control means for operating a two stage, series pump for creating a vacuum in the chamber responsive to a sensed vacuum level in the chamber, wherein said pump is driven by a variable-speed motor, with said control means being designed to operate said vacuum source at a relatively rapid rate during initial pump down, and being further adapted to operate said vacuum source at a substantially steady but lower rate after a desired level of vacuum has been achieved.

4. The apparatus of claim 3 wherein the control means is operable to drive the motor in a first mode of operation in which the motor is driven at a high RPM to evacuate the vacuum chamber and at a low RPM for continuous operation of the degassing unit, a second mode of operation in which the motor is driven intermittently to maintain a set vacuum within the vacuum chamber, and a third mode of operation in which the motor is driven at varying rpms to maintain a constant vacuum within the vacuum chamber.

* * * * *